United States Patent [19]
Edwards et al.

[11] Patent Number: 6,126,613
[45] Date of Patent: Oct. 3, 2000

[54] DEVICE AND METHOD TO MEASURE INHALATION AND EXHALATION AIR FLOWS

[76] Inventors: Raymond A. Edwards; Lucile D. Edwards, both of 304 Tuxedo Sq., Tuxedo Park, N.Y. 10987

[21] Appl. No.: 09/245,589

[22] Filed: Feb. 8, 1999

[51] Int. Cl.[7] ................................................ A61B 5/08
[52] U.S. Cl. .................. 600/539; 600/538; 73/86.77
[58] Field of Search .................... 600/539, 538, 600/533, 532, 531, 529; 73/1.16, 861, 861.352, 861.353, 861.77, 861.92

[56] References Cited

U.S. PATENT DOCUMENTS

| | | | |
|---|---|---|---|
| 4,282,883 | 8/1981 | Yerushalmy | 600/539 |
| 4,441,505 | 4/1984 | Edwards et al. | 600/539 |
| 5,003,828 | 4/1991 | Van Den Burg | 73/861.33 |
| 5,158,094 | 10/1992 | Miller | 600/539 |
| 5,413,112 | 5/1995 | Jansen et al. | 600/539 |

*Primary Examiner*—Cary O'Connor
*Assistant Examiner*—Navin Natnithithadha
*Attorney, Agent, or Firm*—Jay R. Yablon

[57] ABSTRACT

A spirometer is provided which has an air flow path comprising a mouthpiece, filter (such as an air filter or biostatic filter), and an air pathway in which a multiblade transparent windmill rotor rotates when air travels through same. Tips of the rotor are used to detect the rate of rotation providing a train of pulses linearly proportional to the volume of air flowing through the cylindrical air path.

108 Claims, 4 Drawing Sheets

DEVICE AND METHOD TO MEASURE INHALATION AND EXHALATION AIR FLOWS

FIELD OF THE INVENTION

This invention relates to air flow measurement devices, and in particular, to spirometers used to measure inhalation and exhalation.

BACKGROUND OF THE INVENTION

Spirometers are medical instruments which measure inhalation or exhalation flow rates and volumes of the human lung. These typically utilize a rotating device to detect air flows.

However, many spirometers are not realistically designed for the range of applications to which they may be subjected, for example, users with lung infections, or frail users, or users who do not have the capacity to follow verbal directions from a respiratory technician, or use under the direction of a respiratory technician who may not provide proper instruction.

In fact, the results of readings from human-generated air flow can vary as much as twenty percent due to poor inhalation/exhalation maneuvers by the patient, i.e., poor effort and timing of the breath cycle.

Also, the mouthpieces of many spirometers are typically oriented in a manner that makes it more difficult or uncomfortable to properly use and therefor to obtain accurate breathing readings. Similarly, mouthpieces are typically cumbersome to use and do not conform well to the user's mouth.

Known spirometers also do not typically contain adequate safeguards against users who have lung diseases which might contaminate the spirometer, to protect the respiratory technician and subsequent users.

Also, spirometers typically introduce their own resistance and/or back pressure into the air flow path, which can result in inaccurate readings, particularly for a feeble user. Air flow turbulence is also a problem, and can result in reading variations on the order of 15% to 20% for identical air flow rates for a given spirometer calibration.

There are in fact several distinct readings all of which are pertinent to measuring the breathing capacity of the user, which known spirometers typically do not provide as a whole. These include, but are not limited to: total lung volume, peak flow rate, flow rate at the end of a predetermined elapsed time (e.g., one second), and total flow volume after a predetermined period (e.g., fifteen seconds) of multiple breathing maneuvers.

Many spirometers are also of use in a limited range of settings. For example, basic hand-held spirometers often cannot be used in a hospital bedside environment for continuous breathing monitoring. For spirometers used in a hospital setting, the readings taken can sometimes be mismatched with the wrong patient due to personnel errors.

Many spirometers must be held with two hands, and are wired to nearby computation, display and printout devices. The close proximity of these devices as well as the proliferation of wires, may worry or confuse a patient, thus compromising the patient's inhalation or exhalation maneuvers.

In many instances, air expelled through the spirometer blows away from the spirometer user and towards others, which can infect a technician or other person nearby.

Also, spirometers do not typically have a filter with an indicator that would allow someone to determine if that filter has already been used, and thereby prevent reuse of an infected filter.

Multilayer or electronic biostatic filters that might be used for a spirometer are costly to manufacture, and alternatives to this can reduce cost.

Also, the human breath has a comparatively high moisture content with respect to atmospheric air, which acts as a lubricant for the rotating element and distorts the readings of existing spirometers.

Existing spirometers often do not shut down after use, which result in unnecessary power loss. Nor do they provide simple means to calibrate the rotating element.

Finally, because of the filters they employ, existing spirometers are frequently very large, heavy and cumbersome.

OBJECTS OF THE INVENTION

It is therefor an object of the invention to provide a spirometer which is simple, handheld, powered by battery, plus power or solar power, which is inexpensive, and which meets the required physical specifications of the American Thoracic Society for accuracy, pressure drop, and range (i.e. total volume measurement).

It is a further object for said spirometer to provide the measurement results to the user via a digital display and/or fabricated vocal utterances.

It is a further object to provide professional, predetermined voice instructions to the user, via solid state voice-producing components with the spirometer.

It is a further object to configure the mouthpiece, filter, and other components such that they are easily held in the user's hand in a way that is not crowding or intimidating to the user.

It is a further object to provide a filter which is easily placed into the airflow path prior to use, and which may easily be disposed of subsequent to use without hand contact by the respiratory technician thereby protecting the technician and subsequent users from being contaminated by any disease which might otherwise be transmitted from prior users via the filter.

It is a further object to provide a replaceable mouthpiece which conforms easily to the curvature of the lips when the user's mouth is placed around it and which need not be reused by multiple patients and sterilized between uses.

It is a further object to provide a means for decreasing the pressure drop across the spirometer and therefor minimizing resistance and back pressure, thereby improving accuracy.

It is a further object to provide several different types of breathing measurements, for example, but not limited to: total lung volume, peak flow rate, flow rate at the end of a predetermined elapsed time (e.g., one second), and total flow volume after a predetermined period (e.g., fifteen seconds) of multiple breathing maneuvers.

It is a further object to provide means for the spirometer to be adapted to receive signals from a patient "electronic signature" device identifying the patient using the spirometer, and to send this and other signals to a "bedside" receiver for continuous monitoring of a patient's breathing.

It is a further object to provide a spirometer which is small and simple enough to be held and used with only one hand.

It is a further object to provide a spirometer that includes a voice recognition system which eliminates the need for all manual control components other than an on/off switch.

It is a further object to make the rotating element of the spirometer inaccessible to the user, thereby preventing fouling of the mechanical mechanism.

It is a further object to minimize the reading variations that can otherwise occur due to airflow turbulence.

It is a further object to provide a means to prevent potentially contaminated air expelled by the user from being dispersed away from the spirometer and toward another individual, and instead to redirect such air away from individuals other than the user.

It is a further object to provide a filter which indicates whether it has been used before, thereby eliminating the danger that a contaminated filter might be used by and infect a subsequent user.

It is a further object for the filter, when biostatic, to be of a simple design such as a single sheet micro-porous material, thereby reducing manufacturing costs.

It is a further object, to further avoid contamination, to provide an infection-resistant cap fitting over the mouthpiece/filter assembly of the spirometer when it is not in use.

It is a further object to power the spirometer, including its electronic control and detection components, using commercially/available electronics batteries whether rechargeable or not, commercially available plug power supplies, or commercially available solar-powered power devices.

It is a further object to minimize the entry of moisture from the user's breath into the bearings that support the rotation of the rotating element, to minimize the adverse lubrication impact that this moisture may otherwise have on the spirometer readings.

It is a further object to provide a means for simply and accurately adjusting and calibrating the rotating element and the bearings that support this element.

It is a further object to provide a compact, lightweight, user-friendly spirometer.

SUMMARY OF THE INVENTION

A spirometer according to the preferred embodiment of the invention comprises several modular sections, namely, a rotor section, an upper filtration section, a lower filtration section, and a detection and electronics section, a mouthpiece section, and an air outlet section. The rotor speed rotation frequency is determined using either magnetic or optical means to detect when the tips of the rotor blades pass by a rotor rotation detector.

In the preferred embodiment, the modularity of the upper and lower filtration sections allows biostatic filters to be removed and exchanged without hand contact by the user or a technician. The mouthpiece section and a gross matter filter sack associated therewith are similarly modularly removable and exchangeable. The rotor itself is constructed to be more sensitive to inhalation than exhalation since exhalation is typically stronger, and is protected against accidental lubrication by moisture from the patient's breath by humidity guards. It also utilizes a bearing calibration means such as a bearing screw for simple rotor recalibration. The detection and electronics section is also separate from the remaining mechanical sections of the device, so that the rotor and other mechanical parts—which can become worn or contaminated—are disposable independently. The spirometer electronics tracks air flow per time over a period of time, so that a wide range of pertinent breathing data may be further deduced. An optional air composition detector is used to obtain data for analyzing the content of exhaled air in comparison to the ambient air, particularly but not limited to carbon dioxide and oxygen. Further options, variations and embodiments are described in more detail below.

BRIEF DESCRIPTION OF THE DRAWING

The features of the invention believed to be novel are set forth in the appended claims. The invention, however, together with further objects and advantages thereof, may best be understood by reference to the following description taken in conjunction with the accompanying drawing(s) in which:

DETAILED DESCRIPTION OF THE PREFERRED EMBODIMENT OF THE INVENTION

Figure 1:
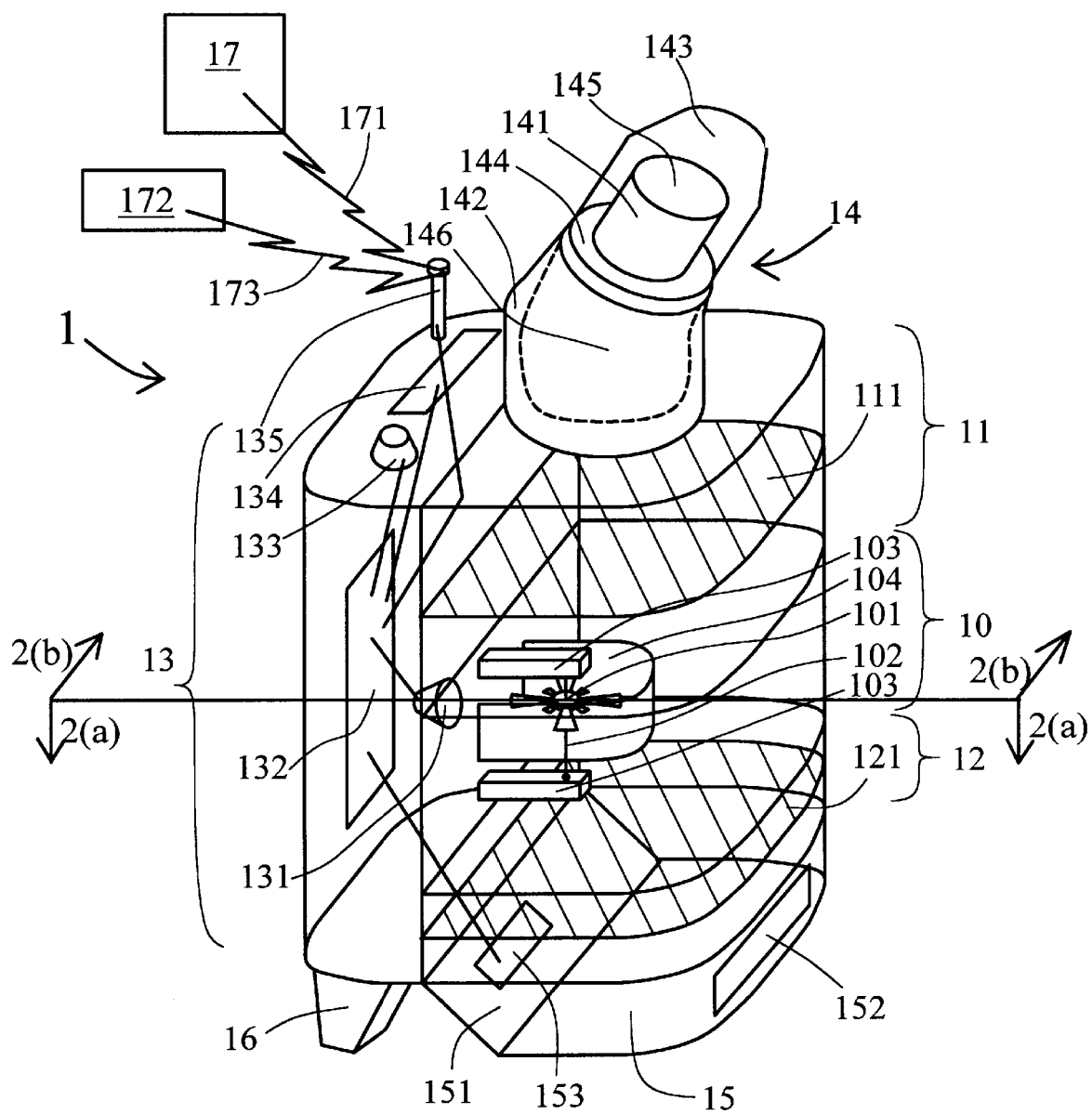
FIG. 1 is a perspective view illustrating the preferred embodiment of the invention, with transparency as necessary to make visible some of the inner components of the invention.

FIG. 1 illustrates the preferred embodiment of the invention in perspective view. Spirometer 1 according to the preferred embodiment comprises four main modular sections, namely, rotor section 10, upper filtration section 11, lower filtration section 12, and detection and electronics section 13. Also illustrated are mouthpiece section 14, air outlet section 15, and electronics section support legs 16 (only one shown, one or more others hidden), which may or may not be distinct modules relative to the four main modular sections to which they are adjacent.

Mouthpiece section 14 further comprises mouthpiece means 141 attached to a tilted, rotatable neck section 142. Mouthpiece 141 should be of an appropriate size to be comfortably placed into the user's mouth for exhalation or inhalation as desired, and different sizes and shapes may be used, for example, for children or people of different mouth sizes. This tilt in neck 142 makes it easier to use spirometer 1 and also to read the digital display and operate the spirometer, as will be discussed further. Similarly, the rotation allows mouthpiece 141 to be stored compactly for boxing and shipment, especially in combination with mouthpiece cap 143 to be next discussed. Covering mouthpiece 141 is removable mouthpiece cap 143 which maintains mouthpiece 141 in a sanitary condition prior to use and prevents particulate and other contaminants from falling into spirometer 1. Mouthpiece 141 sealably attaches to and detaches from neck section 142, for example, by screwing onto and unscrewing off of neck section 142 using mouthpiece-to-neck attachment means 144, with an appropriate airtight seal proximate where mouthpiece 141 meets neck 142. Gross matter filter sack 146 is also attached beneath mouthpiece 141 proximate mouthpiece-to-neck attachment means 144, and comprises apertures wide enough to allow air to flow freely though it but small enough to trap and stop particulate matter (e.g., food bits, phlegm, saliva) from entering upper filtration section 11 and the rest of spirometer 1. This keeps the spirometer clean from debris which might otherwise cause it to obtain inaccurate readings.

Preferably, gross matter filter sack 146 is fabricated from a moisture-sensitive material that turns color when contacted by moisture. For example, filter sack 146 can be impregnated or dusted with certain vegetable dyes or chemicals that change color when exposed to moisture. In this way, when an individual exhales through his or her mouth into mouthpiece 141 and through filter sack 146, the moisture from that person's breath will cause filter sack 146 to change color, thus indicating that the particular mouthpiece 141 and sack 146 combination has already been used. This, coupled with the removability of mouthpiece 141 from neck section 142, allows a new mouthpiece 141, cap 143 and filter sack 146 to be used for each individual patient, and averts the situation where new mouthpiece 141 and filter sack 146 are inadvertently reused, further enhancing sanitary condition. Optimally, mouthpiece 141, cap 143 and sack 146 are supplied as a separate, one-use, disposable assemblage. It is understood that a range of options may be available in the art for producing the aforementioned color change effect, and so the use of any apparatus or method which is known or may become known in the art to alter the filter sack 146 coloration in response to moisture is considered within the scope of this disclosure and its associated claims.

Air blown into mouthpiece opening 145 of mouthpiece 141 passes through mouthpiece 141 and neck section 142, through filter sack 146, and into upper filtration section 11. Upper filtration section 11 preferably comprises optional upper biostatic filtration means 111 therein and integrally affixed thereto. Biostatic filter 111 is used to prevent cross-contamination in a clinical or hospital setting. While many types of complex and expensive embodiments may be used for biostatic filter 111, including filters with multiple layers and materials, as well as filtering electronics, the preferred, lowest cost embodiment is a single, lightweight biostatic "accordion sheet" with microscopic pores. Such a filter greatly reduces the overall size and weight of spirometer 1, making it much more user-friendly. Because of this integral affixation between upper biostatic filter 111 and upper filtration section 11, and because upper filtration section 11 is modular, upper biostatic filtration means 111 can easily be removed from spirometer 1 and replaced simply by removing and replacing upper filtration section 11. Importantly, this can be achieved without the person (e.g., technician) who removes upper biostatic filtration means 111 ever having to directly touch upper biostatic filtration means 111, and is thus a further sanitary benefit according to the invention.

Air passing through upper filtration section 11 next enters rotor section 10, which comprises the primary mechanical hardware which is actuated by air flow through the spirometer. This hardware, which will be discussed in more detail in connection with FIG. 2, comprises rotor means 101 oriented perpendicularly to the flow of air (similarly to a "windmill," as opposed to parallel to the flow in a "water wheel"-type design) as shown, rotor spindle 102 rotatably attaching rotor means 101 to rotor support housings 103, and rotor turbulence barrier 104 surrounding rotor means 101 as illustrated. These are all affixed to a rear wall of rotor section 10 as shown, and as will be discussed further below, this rear wall must be transparent in the event that optical detection is used, and permeable by magnetic flux in the event that magnetic detection is used. Rotor turbulence barrier 104 is important, because as noted above, the turbulence of air flowing through a spirometer and past the rotor can cause even properly-calibrated readings to vary by perhaps 15% to 20%. Rotor turbulence barrier 104 is essentially a narrow tube that surrounds rotor means 101 and "disciplines" the air flowing through the tube and past the rotor so as to reduce turbulence variation to perhaps only 1% to 2%. Thus, once spirometer 1 has been properly calibrated, reading variations for a given air flow will be negligible and the results highly reproducible. Air flow is of course measured based on detecting the rotational frequencies with which rotor means 101 rotates at various identified times as well as over time, as will also be further discussed in connection with FIGS. 2 and 3.

Once exhaled air has left rotor section 10, it finally enters into and passes through lower filtration section 12. Similarly to upper filtration section 11, lower filtration section 12 preferably comprises optional lower biostatic filtration means 121 therein and integrally affixed thereto. Again, because of this integral affixation, and because lower filtration section 12 is also modular, lower biostatic filtration means 121 can also easily be removed from spirometer 1 and replaced simply by removing and replacing lower filtration section 12. Importantly, once again, this can be achieved without the person who removes upper biostatic filtration means 111 ever having to directly touch upper biostatic filtration means 111, and is thus yet a further sanitary benefit of the invention. It is to be noted that the two biostatic filters 111 and 121 are preferred, but optional. One or both of these may be omitted as desired, and in that event, the corresponding modular section 11 or 12 is simply an air pass-through section. Because of the modular nature of these sections, upper and lower biostatic filters 111 and 121 can be so-included or omitted at will, in any combination.

At the lower extremity of lower filtration section 12 is air outlet section 15, which preferably is integrally affixed thereto, but which may optionally be yet another removable, interchangeable module. Airflow diversion means 151 such as the tilted face shown, coupled with horizontally-directed air outlet opening 152 as shown, and further coupled with the orientation of the mouthpiece 141 via tilted rotatable neck section 142 as shown, will cause exhaled air to exit spirometer 1 through air outlet opening 152, directly toward the user's lower body. This is more sanitary than having air expelled out of the spirometer away from the user, which often means that it is simultaneously expelled toward someone else (e.g., the technician) who can then be infected by this expelled air. This is yet another sanitary benefit of the invention, and this is another reason why neck section 142 is tilted.

Spirometer 1 also optionally comprises an air composition detector 153 (or means to attach such detector 153) that obtains data to analyze the content of exhaled air in comparison to the ambient air, particularly but not limited to carbon dioxide and oxygen. This is preferably located within lower filtration section 12 and/or air outlet section 15, though it can be placed at any practical location in the airflow path within the scope of the invention and its associated claims. The information obtained from air composition detector 153 is useful to determine the efficiency with which the patient's lungs are absorbing oxygen and emitting carbon dioxide and other waste gases. The detector detects both the patient's exhaled air, as well as the ambient air, so that a baseline may be established to determine how the air composition is being changed within the patient's lungs and body. Any air composition detector 153 that is known or may become known in the art is suitable for this purpose.

It is important to point out at this juncture, while the foregoing description summarizes the air flow path through spirometer 1 from top to bottom for user exhalation, that spirometer 1 is equally useful for measuring inhalation, and that the invention as further described below serves to provide measurements in both situations that meet or exceed industry accuracy standards. For inhalation, the air flow is simply reversed, such that air enters through air outlet opening 152, then passes through lower filtration section 12, rotor section 10, and upper filtration section 11. Finally, the inhaled air will pass through rotatable neck section 142 and mouthpiece 141 into the user's mouth and lungs. Gross matter filter sack 146 in its preferred embodiment is ribbed and comprises a reasonably stiff neck, so that it is not sucked up into the user's mouth during inhalation. Gross matter filter sack 146 can also be removed for inhalation maneuvers if desired, though its presence can prevent any unexpected loose matter within the spirometer from accidentally being inhaled and choking the patient. Typically, inhalation and exhalation are a separate series of tests, that is, one either does a series of one or more tests involving inhalation, or a series of one or more tests involving exhalation, as opposed to both inhaling and exhaling during a single test or series of tests.

Finally, detection and electronics section 13 comprises rotation detector 131 which detects the rotation speed of rotor means 101, a computerized device 132 comprising appropriate computer hardware chips and boards and/or software. Among its other functions, computerized device 132 receives information from rotation detector 131 and calculates information such as air flow rates and volumes at and over specified times. It also receives signals from activation means 133 such as the touch-button illustrated, and communicates with an information input/output device 134 which, for example, displays (or vocalizes) use instructions and/or the desired reading information based on the detected air flow, and which also optionally receives and recognizes voice input signals that control spirometer 1 operation.

Also illustrated is a communications link 171 between a wireless transmitter 135 of spirometer 1 and a bedside receiver 17 which, in its preferred embodiment, is a (short-range) wireless or optical link, but which may also be a wired connection in an alternative embodiment. This enables data gathered by spirometer 1 in a hospital or similar patient facility to readily be fed to other computerized equipment used by that facility to monitor and further analyze a patient's condition. In addition, to prevent spirometer readings from being recorded in connection with the wrong patent, patients may be provided with an optional electronic signature device 172 such as a card or similar device known in the art. Spirometer 1 detects this signature information via signature link 173 again using devices and methods known in the art, and conveys it along to bedside receiver 17 via communications link 171 along with the data captured by the spirometer's breathing readings. Wireless links are preferred for all of this to reduce nearby wiring; but this does not preclude the use of direct (non-wireless) links within the scope of the invention.

Lines in FIG. 1 connecting computerized device 132 with rotation detector 131, activation means 133, information input/output device 134, wireless transmitter 135, and air composition detector 153 are included to schematically illustrate the interconnection and flow of information between and among these components. Detection and electronics section 13 will of course also have a power source 302 (see FIG. 3) using, for example, a battery (preferably), or a power plug, or a solar cell (if enough light is available), such as are conventionally used in similar electronics applications. The overall electronic operation of spirometer 1 will be illustrated and discussed in detail in connection with FIG. 3.

The modularity of electronics section 13 is important, so that this section can be separated from the mechanical sections (10, 11, 12, 14, 15) through which the air flows while these latter sections are sterilized, or discarded and replaced. Thus, the electronics section is reusable throughout numerous replacements of one or more of the other sections. As will be discussed further below, while the rotor means 101 is housed in rotor section 10, rotation detector 131 is housed fully separately and removably therefrom in electronics section 13.

Electronics section support legs 16 (which may be separate modules, or may alternatively be affixed to and integral with detection and electronics section 13) simply support detection and electronics section 13 such that entire spirometer 1 can be rested on a flat surface and remain upright. Thus, it should be apparent that these legs 16 can be varied in a wide range of obvious configurations within the scope of the invention.

Earlier, examples were given of how the mouthpiece section 14 may be attached to the remainder of spirometer 1, as well as how the components comprising mouthpiece section 14 may be attached to one another. The modularity of spirometer 1, and in particular the attachment and detachment of the remaining various modular sections such as the rotor section 10, upper filtration section 11, lower filtration section 12, detection and electronics section 13, and air outlet section 15 to and from one another, can be achieved using a variety of attachment means and methods well known in the art. For instance, sections can have complementary mated grooves that allow them to slide together and then snap into place, as well as means to later enable separation of the sections. Some form of substantially airtight seal is also desirable at the point of contact between sections. Alternatively, a "slotted" frame may be used, with the modular sections 10, 11, 12, 13, 14, 15 simply sliding into this frame in the appropriate location in the frame much as individual furniture drawers are slid into and out of the frame for a drawer chest or computer boards are slid into and out of computer slots. Again, between adjacent sections, holding, sealing and release means are desirable to hold and seal the sections together, and to later release them for separation. Alternatively, depending on the shapes of the sections (it is pointed out that the shapes shown in FIG. 1 are illustrative but that other shapes which achieve the same end are equally within the scope of the invention), it may be possible to simply screw one section into the next using complementary threading and seals, in the rotational manner widely used in many applications. And, indeed, any other means and methods of attachments known in the art that might be used to attach and substantially seal these modular sections together so as to achieve the overall modularity heretofore described, and to enable their later detachment from one another, are suitable for use according to the invention and are within the scope of this disclosure and its associated claims.

FIG. 2(*a*) is a top, and 2(*b*) is a side cross sectional view of the rotor mechanism and the associated rotation detector mechanism according to the invention, taken from the 2(*a*)—2(*a*) and 2(*b*)—2(*b*) section lines of FIG. 1. Between the two views is a side view illustrating the pitch of the rotor means 101 blades.

FIG. 2(*a*) shows rotor section 10 and detection and electronics section 13. As discussed above, rotor means 101 resides within rotor turbulence barrier 104 which minimizes turbulence and maximizes reproducibility. Rotor means 101 preferably accounts for no more than about 25%, and generally no more than between 10% and 30% of the overall cross sectional area within turbulence barrier 104, so that the remaining area is open to air flow. Additionally, of course, air will flow through the cross sectional region of rotor section 10 outside of turbulence barrier 104. This configuration thus minimizes the pressure drop across the rotor and thus the patient effort required to activate the rotor and enables accurate readings, even for patients with very limited breath capacity.

It is also to be observed that if rotor means 101 is of a size and weight that readily maintains its angular momentum, that readings will be less accurate since rotation detector 131 will still detect rotation even after the airflow has ceased. Thus, rotor means 101 should be fairly small and lightweight, so as to introduce negligible momentum of its own.

Figure 2A:
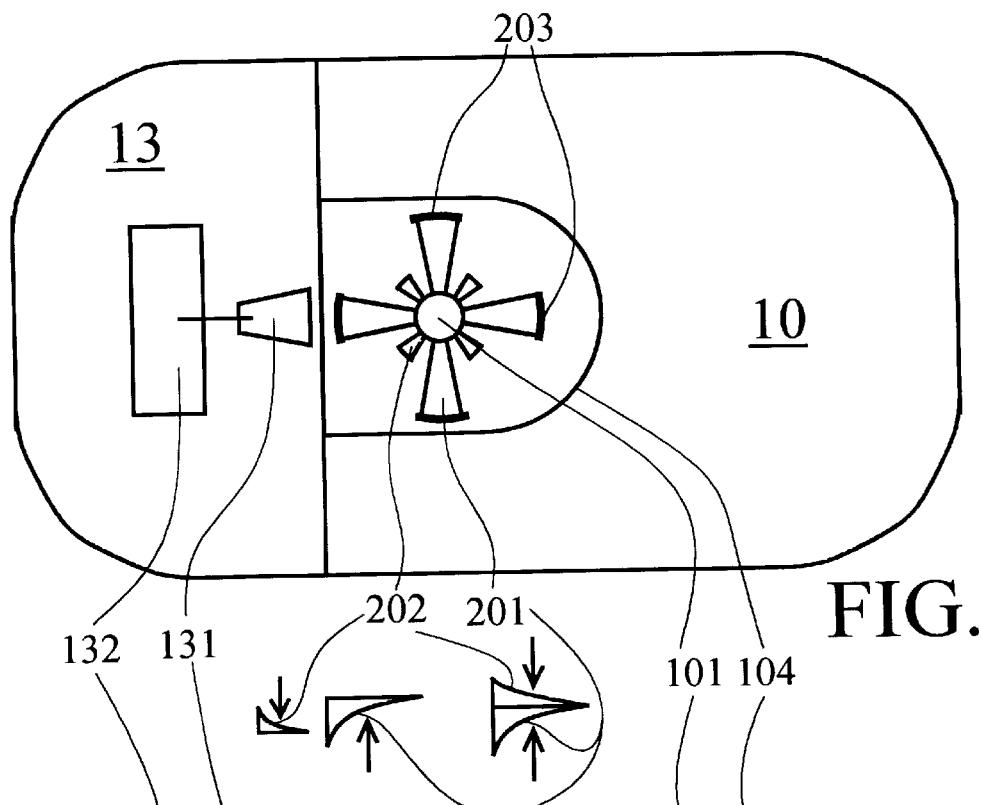
FIGS. 2 illustrate a top and side cross sectional views of the rotor mechanism and the associated rotation detector mechanism according to the invention.
Figure 2B:
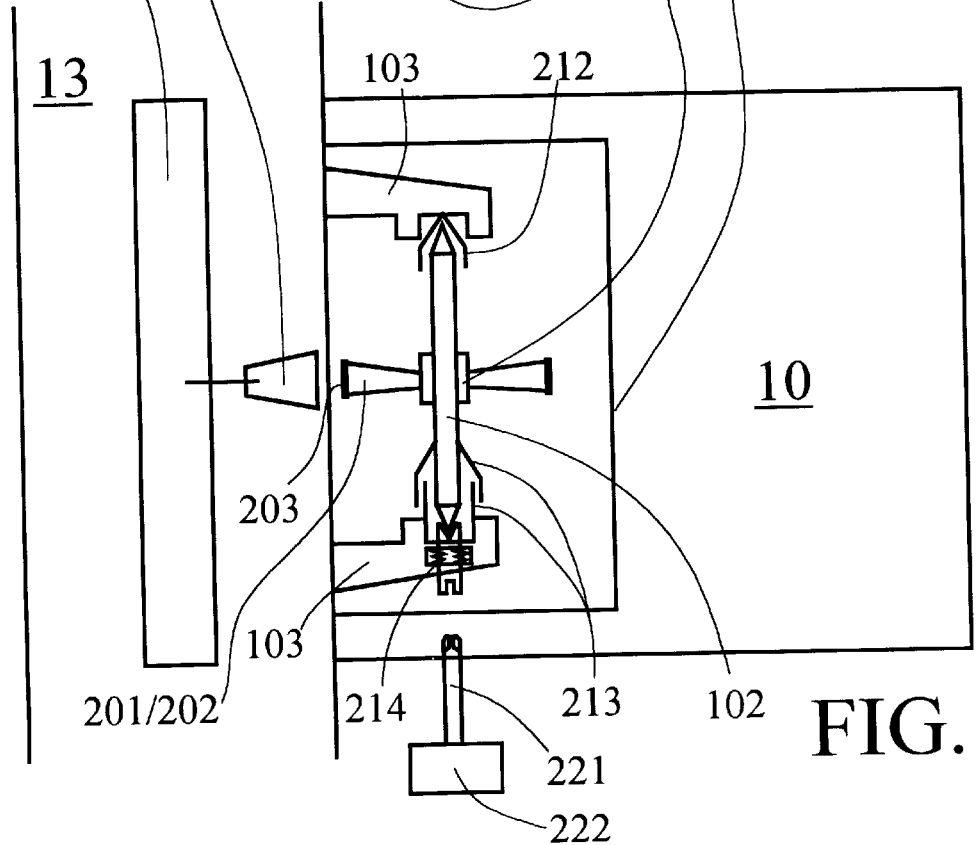

Because the air pressure that most people generate from exhalation is stronger than that which they generate from inhalation, the blades faces used to spin rotor 101 for inhalation need to be more sensitive (reactive to air flow) than those used to spin it for exhalation. On general aerodynamic principles, there are two basic options to achieve this, namely, i) for a given blade pitch, providing a larger blade surface area for inhalation than for exhalation, or ii) for a given blade surface area, providing a higher, more sensitive blade pitch for inhalation than for exhalation. As illustrated in FIG. 2(a), rotor means 101 has a plurality of separate larger inhalation rotor blades 201 and smaller exhalation rotor blades 202, each with similar pitch, which corresponds to the former option i). Between FIGS. 2(a) and 2(b), the leftmost drawings illustrate the pitch of these two sets of blades, denoting how the smaller blades 202 are pitched to be activated only by exhalation (downward arrow) and the larger blades 201 to be activated only by inhalation. For the latter option ii), one has but a single size of blade, and the rightmost drawings between FIGS. 2(a) and 2(b) illustrate how this single blade size has a higher, more sensitive pitch for inhalation (upward arrow) than for exhalation (downward arrow). A rotor 101 configured according to one of these two options, or a mix of these two options, shall be referred to generally as a flow-direction asymmetric rotor, which in this case discriminates in favor of (is more sensitive to) inhalation over exhalation.

Detecting the rotational frequency of rotor means 101 is performed either magnetically or optically. In either case, the tips of at least one blade 201, 202 comprise a detection surface 203. For magnetic detection, detection surface 203 comprises a magnetic substance upon or integrated with at least one, and preferably at least two opposite outer blade tips, and rotation detector 131 comprises a magnetic pickup to detect each time the magnetic substance passes by, using magnetic detection means well known in the art. For optical detection, detection surface 203 comprises an optically-reflecting substance upon or integrated with at least one, and again preferably at least two opposite outer blade tips, and rotation detector 131 comprises an optical emitter and receiver to similarly detect each time the optically-reflecting substance passes by, using optical detection means well known in the art. Thus, for magnetic detection, the boundary between rotor section 10 and detection and electronics section 13 must comprise a material that allows (i.e., does not block) magnetic flux from the blade tip to pass therethrough and be picked up by detector 131 (or be open), while for optical detection, this boundary must allow (i.e., not block) passage of the optical signal to detector 131 and therefor should generally be transparent (or open).

For optical detection, infrared emission and detection is a preferred embodiment, but is not the only option. Other electromagnetic frequency spectra can similarly be used and are equally within the scope of the invention. In all cases, rotation detector 131 sends a detection signal to computerized device 132 each time a blade detection surface 203 passes by, and computerized device 132 performs the necessary calculations to transform that raw information into the desired end-user information regarding air flow rates, volumes, etc.

FIG. 2(b) is a side cross-sectional of rotor means 101 and its supporting mechanisms. Rotor means 101 is connected to and rotates integrally with rotor spindle 102. The tips of spindle 102 are finely sharpened for maximum sensitivity. Upper and lower rotor support housings 103 support rotor means 101 and spindle 102 as shown and provide a stable rotational origin for rotor 101, and spindle 102 rotates within and contacts housings 103 at its tips.

It is to be particularly observed that as a spirometer is used, moisture from the user's breath can enter the spirometer and serve to lubricate the rotation of the spindle 102 at its tips, which compromises the reproducibility of the readings by making the spirometer more sensitive (reactive) to air flow once sufficient moisture has accumulated therein.

To avoid this, upper 212 and lower 213 humidity guards are also introduced as shown, which deters moisture from entering the region at the contact points where the spindle 102 tips contact support housings 103. Upper guard 212 is integrally affixed to upper housing 103 and—since exhalation air enters spirometer 1 from above—is oriented in an inverted-v as shown to prevent entry of moisture from above. Lower guard 213 actually has two elements. First, a second inverted-v is integrally affixed to the lower region of the spindle as shown, again, to block moisture entering from above. Second, an upright-u that at its upper region is bounded by this second inverted-v is integrally affixed to the lower housing 103 as shown. As can be seen, this configuration, or equivalent configurations that may be apparent to someone of ordinary skill, serves to keep humidity from accumulating near the spindle 102 tips, thus maintaining reproducibility of the spirometer readings.

It is also to be observed that from time to time, it may be necessary to recalibrate spirometer 1, that is, to finely adjust how easily rotor means 101 rotates in response to a given air flow. This is achieved, as one example, by means of a lower bearing calibration means 214 such as the illustrated bearing screw (phillipshead or otherwise), which can be moved slightly up or down as desired to tighten or loosen the spindle and thus adjust the sensitivity of rotor 101 with respect to any given airflow. To access calibration screw 214, an opening beneath the spirometer may be introduced through which a screwdriver 221 can pass. Or, this can be adjusted while rotor section 10 is disconnected from the spirometer. Screwdriver 221 may be manually operated, or for higher accuracy, is controlled by computer-based calibration server means 222 which precisely controls rotation of screwdriver 221 and hence rotor 101 calibration. Preferably, jewel-quality bearings are used at the locations where the spindle 102 tips spin, since these afford maximum sensitivity. It is also to be noted that the overall mechanism comprising rotor 101, spindle 102, support housings 103 and the various guards and bearings described above, if desired, may optionally be provided as a distinct module attachable to and removable from the overall rotor section 10.

Figure 3:
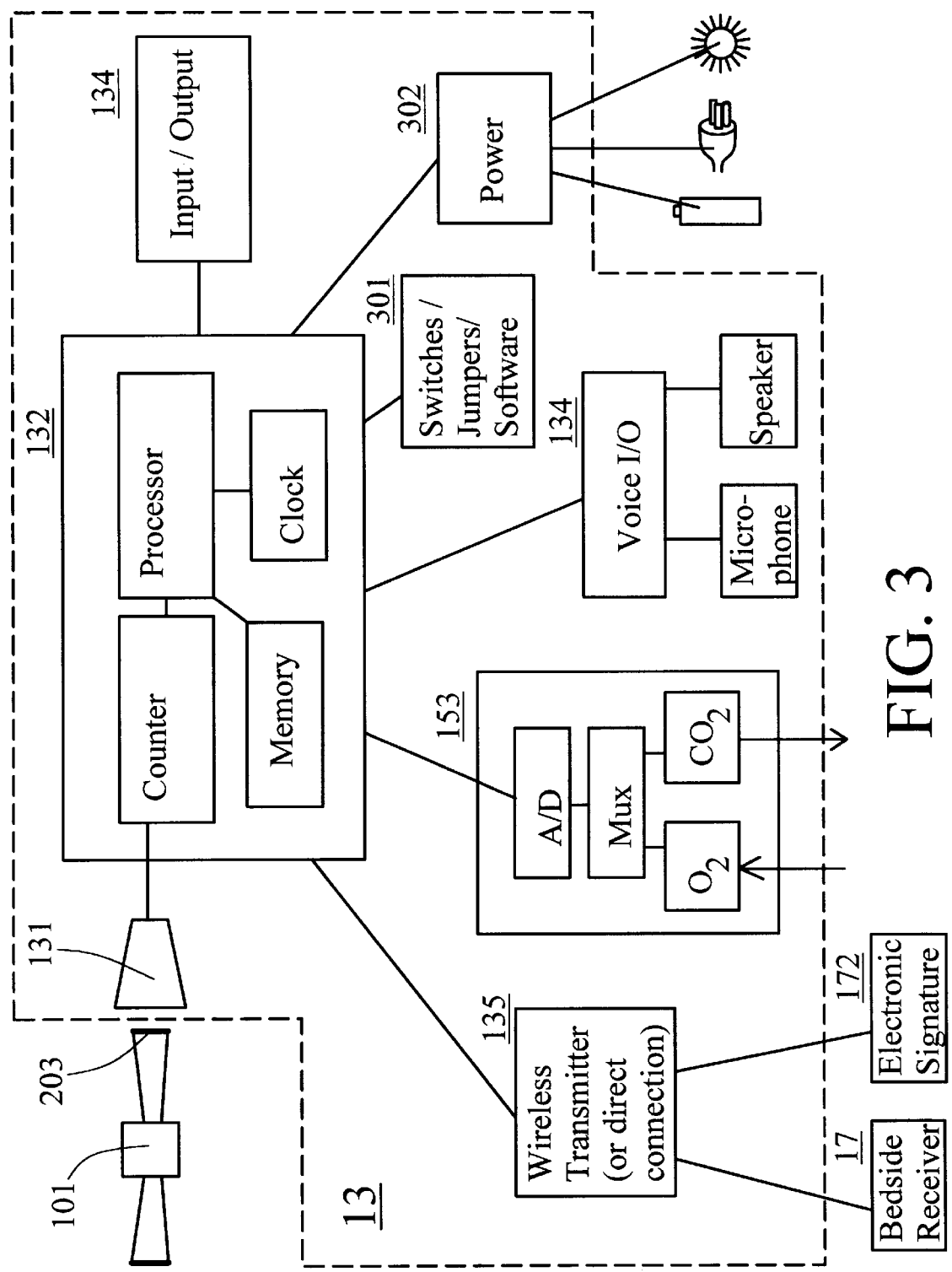
FIG. 3 is a block diagram illustrating the overall electronic configuration and operation of the spirometer according to the invention.

FIG. 3 illustrates the overall operation of the electronics within detection and electronics section 13. Detection surface(s) 203 of the rotor 101 blade tip(s) move past rotation detector 131 as earlier described. Computerized device 132 comprising a processor, counter, clock, and necessary memory for data storage receives each "pulse"

indicating that a detection surface 203 has passed detector 131. These discrete pulses are counted by the counter and related to a signal from the clock, so that the rate of revolution (spin frequency) of rotor means 101 may be calculated by the processor. This frequency may of course be recorded not just at a given time or times, but also over time. The processor then uses this frequency information to calculate both air flow rates at one or more predetermined times, as well as air flow volumes during one or more predetermined time periods. The results of these calculations are then displayed on input/output device 134, which as noted earlier, can be a visual display, and/or can be a voice "display" using a speaker. A voice system may also contain prerecorded instructions to walk the user through the use of spirometer 1, thereby obviating the need for a technician and allowing spirometer 1 to be employed as a personal use device. Computer 132 may also me adjusted by means of various jumpers or switches and/or controlled by a software interface 301. Power is provided by power source 302 which may include, for example, battery, electric, or solar power. Information from electronic signature device 172 is transmitted to computer 132, and information from computer 132 is transmitted to bedside receiver 17 via wireless transmitter 135, as earlier discussed. Finally, optional air composition detector 153, which may be detachable from or integrated with spirometer 1, detects the ambient and exhaled air content including oxygen and carbon dioxide levels, and this too is provided to computer 132 so that the desired readings may be calculated and provided 134 to the technician and/or the user. It is understood, of course, that the exact divisions of function illustrated by FIG. 3 are merely illustrative, and that any combination of known elements that produces some or all of the functional results described by FIG. 3 is considered within the scope of this disclosure and its associated claims.

Figure 4:
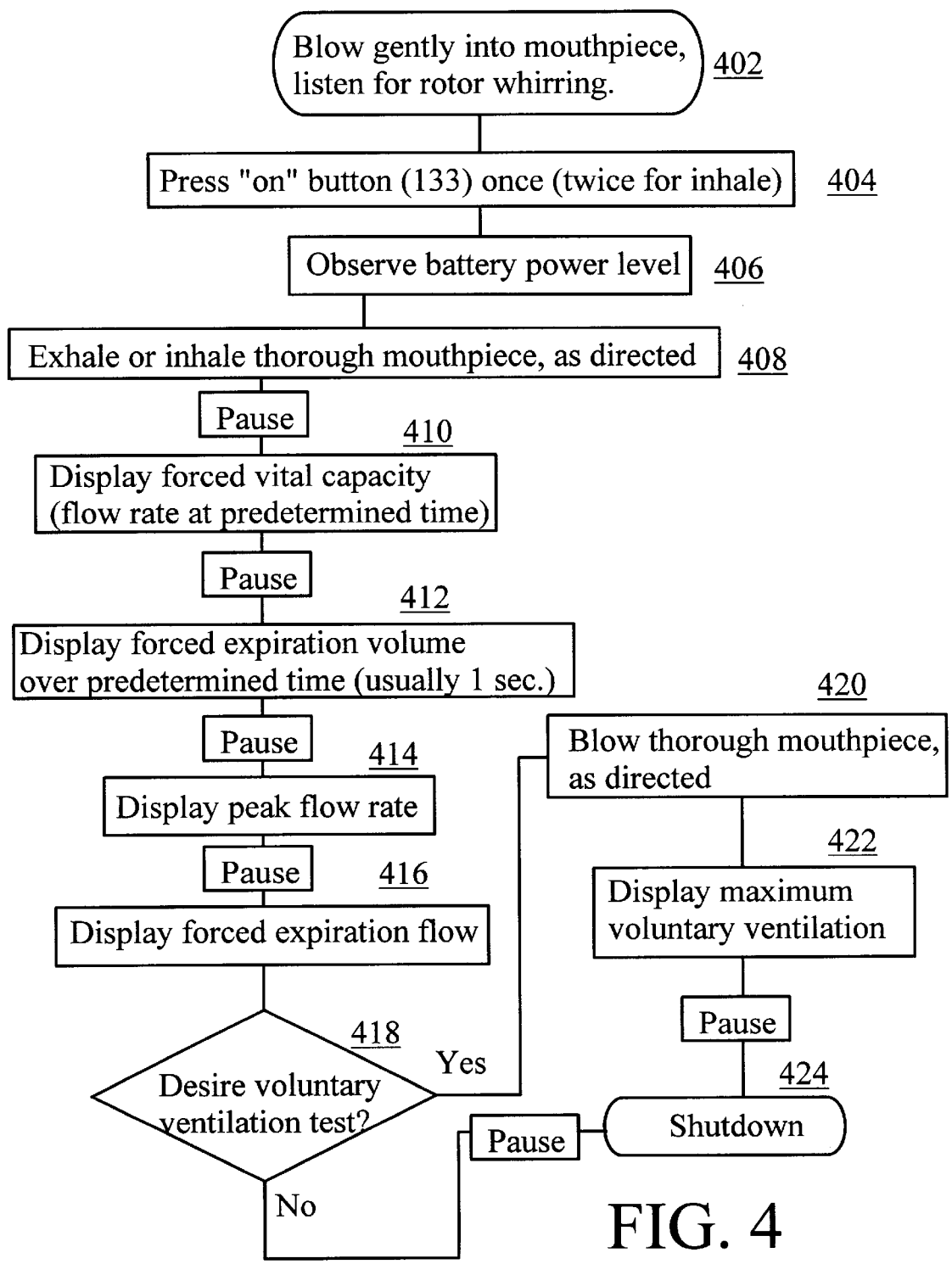
FIG. 4 is a flowchart showing the activation and use sequence for the preferred embodiment of the invention.

FIG. 4 shows a sample activation sequence for the preferred embodiment of the invention. In the preferred embodiment, input/output device 134 is a single display screen (e.g. LED) and/or a speaker for voice, and so a series of displays or utterances are used to communicate pertinent data. Once spirometer 1 has been assembled from its modular components as earlier described, the user removes cap 143 and begins the activation sequence by removing blowing gently into mouthpiece 141. If the whirring of the rotor is heard, then the unit is ready for use. (402) Activation means 133 such as the touch-button illustrated is then utilized to turn on the spirometer 1. (404) A single actuation of activation means 133 (e.g. a single press of the button) signals that exhalation is to be monitored, while a time-limited double actuation (e.g., a double press of the button within a short period of perhaps under 3 to 5 seconds) signals that inhalation is to be monitored. A power indicator (not shown) is observed to make certain that spirometer 1 has necessary power available to it. (406) At that point, following directions which may be provided by the speaker for the voice embodiment (see FIG. 3) and which are otherwise provided by a technician or other means, the user exhales or inhales (408) thorough mouthpiece 141. During this time, rotation of rotor 101 is detected 131 and the data resulting therefrom is analyzed by computer 132 and stored. Typically, computer 132 will maintain data that can be used to chart the air flow rate (air volume per time) as a function of time (essentially a mathematical curve of volume per time versus time), and so has available the necessary data to determine the flow rate at one or more specified times, as well as to determine the total flow volume over a period of time (which mathematically is the integral under this curve, between two specified times). The flow rate versus time curve actually comprises discrete points separated from one another along the time axis by the time between successive passes of each detection surface 203 past detector 131. Since this is typically on the order of a small fraction of a second, this curve can thus be regarded as continuous for all practical purposes, and calculations of flow rates and volumes at or between distinct predetermined times can be regarded as calculations of data at or between substantially instantaneous times. (That is, the discrete detected pulses are so close together temporally, that this discreteness can be disregarded and treated as continuous.) If wireless link 171 to bedside monitor 17 is established, or in optional, more sophisticated embodiments of the invention, this information can be plotted and displayed graphically if desired.

Once the breathing has ceased (i.e., rotor 101 has substantially stopped), there is a pause of perhaps five to ten seconds, at which point input/output device 134 will output the patient's forced vital capacity (FVC)(410), which is typically a measure of flow rate substantially about one second after the breath was initiated, though any predetermined time can be selected using switches/software 301 discussed earlier. Mathematically, this is value of the flow rate, at a given time along the flow rate versus time curve. This would include some indication (visual or audible) that the number being output is in fact the FVC. After another similar pause, the forced expiration volume (FEV) is similarly displayed (412), along with an indication that this is what is being displayed. This measures the total volume of air expelled during a predetermined time, typically during the first second of breathing, but again, this can be adjusted to provide total air volume as between any two predetermined times. Mathematically, this is the area under (integral of) the curve between two specified times. Following a further pause, the peak expiration flow rate (PEF) is displayed (414), which represents the maximum point (first derivative=0) on the flow rate versus time curve. Next, after a pause, the forced expiration flow rate (FEF) is displayed (416), which is the average rate of flow over a specified time period, usually during the middle half of the FEV period (typically about 25% to 75% of the way through the FEV period). (Total volume, i.e. area under the curve, during specified time period, divided by specified time period.) Finally, the display sequence ends, and unless a maximum voluntary ventilation (MVV) test is desired, the spirometer 1 power will shut down (424) after one last pause of perhaps twenty or thirty seconds. The unit can also shut down any time activation means 133 is actuated while the unit is on, other than the double actuation used to signal inhalation. If an MVV is desired (418), the user will again blow through the mouthpiece as instructed (420) and the MVV (422) will be displayed similarly to the other earlier results. The MVV, which is often used for athletes or individuals in good physical condition, measures the largest volume of air (area under the curve) that can be breathed over a specified time (usually fifteen second) by forced voluntary effort.

The aforementioned describes but one of many ways in which the patient's breathing data can be monitored and output according to the invention, and it is understood that a wide variety of display methodologies that would be apparent to someone of ordinary skill are available within the scope of this disclosure and its associated claims. It is also understood, that once the data curve showing flow rate (air volume per time) as a function of time is calculated and maintained within computer 132, that many varying calculations can be made and output provided based on this data using various points along the curve, and various integral and derivative calculations based on that that curve. Any such calculation that may reasonably be performed from this data curve is thus considered to be within the scope of this invention and its associated claims. Finally, for embodiments of the invention that include air composition detector 153, it is understood that the data displayed may also include information regarding the air composition of ambient versus exhaled air, both independently of the air flow data, and in relation to the air flow data, in any combination desired.

While only certain preferred features of the invention have been illustrated and described, many modifications and changes will occur to those skilled in the art. It is, therefore, to be understood that the appended claims are intended to cover all such modifications and changes as fall within the true spirit of the invention.

We claim:

1. A spirometer apparatus for measuring airflow therethrough generated by a user thereof, comprising:
    a rotor comprising a plurality of rotor blades;
    a mouthpiece enabling said user to breathe air through said spirometer thereby creating said airflow therethrough;
    an air outlet opening enabling exhaled air to exit said spirometer and inhaled air to enter said spirometer;
    at least one detection surface comprising part of at least one of said plurality of rotor blades;
    a rotation detector detecting passage of said at least one detection surface past said rotation detector and generating a detection signal in response thereto;
    a computerized device receiving said detection signal, and using said detection signal to measure said airflow through said spirometer; and
    a rotor turbulence barrier surrounding said rotor, wherein a rotor cross-sectional area of said rotor occupies no more than 30% of a barrier cross-sectional area of said rotor turbulence barrier, and wherein air that does not flow through said rotor turbulence barrier is enabled to flow through a remaining cross-sectional area within said spirometer outside of said rotor turbulence barrier, thereby reducing turbulence of said airflow past said rotor while minimizing pressure drop across said rotor.

2. The apparatus of claim 1, further comprising:
    a modular detection and electronics section comprising said rotation detector and said computerized device;
    a modular rotor section separate from said modular detection and electronics section, and comprising said rotor and said at least one detection surface of said tip of at least one of said blades; and
    boundary means between said detection and electronics section, and said rotor section, allowing said rotation detector to so-detect, and not blocking said rotation detector from so-detecting, each said passage of said at least one detection surface past said rotation detector.

3. The apparatus of claim 1, wherein said rotor is aerodynamically flow-direction asymmetric so as to provide greater sensitivity to inhalation over exhalation.

4. The apparatus of claim 1, further comprising:
    a rotor spindle further comprising upper and lower spindle tips, connected to and rotating integrally with said rotor;
    upper and lower rotor support housings contacting said upper and lower spindle tips respectively, within which said rotor spindle rotates, supporting and providing a stable rotational origin for said rotor; and
    upper and lower humidity guards proximate contact points where said upper and lower spindle tips respectively contact said upper and lower rotor support housings, deterring moisture due to said user's exhalation airflow from adversely lubricating said contact point and thereby undesirably causing the rotor to become more sensitive to any given airflow.

5. The apparatus of claim 1, further comprising:
    a rotor spindle further comprising upper and lower spindle tips, connected to and rotating integrally with said rotor;
    upper and lower rotor support housings contacting said upper and lower spindle tips respectively, within which said rotor spindle rotates, supporting and providing a stable rotational origin for said rotor; and
    bearing calibration means for adjusting the tightness with which said spindle and said support housing contact one another and thus the sensitivity of said rotor with respect to any given airflow.

6. The apparatus of claim 1, further comprising:
    gross matter filter sack means proximate said mouthpiece, enabling air to flow freely while preventing particulate matter from passing therethrough into said spirometer, and providing indicator means activated in response to contact by moisture from a user's breath to indicate if said filter has already been used.

7. The apparatus of claim 1, further comprising at least one removable and replaceable modular filtration section comprising at least one biostatic filter therein and integrally affixed thereto, providing means for a person to remove and replace said at least one filtration section and said at least one biostatic filter thereof without directly contacting said at least one biostatic filter.

8. The apparatus of claim 7, wherein said at least one biostatic filter is comprised of a compact, lightweight, microporous, accordion-type biostatic material enabling said spirometer to be compact and lightweight.

9. The apparatus of claim 1, wherein said mouthpiece and said air outlet opening are oriented and positioned with respect to said spirometer such that the exhalation airflow from the spirometer user exits said air outlet opening toward said user's lower body, and does not exit away from the user and toward any other individuals who may be positioned in front of the user.

10. The apparatus of claim 1, additionally for measuring the composition of said airflow, further comprising an air composition detector obtaining data regarding the composition of air exhaled into the spirometer in comparison to ambient air, and providing said data to said computerized device for any desired computation and subsequent output.

11. The apparatus of claim 1, further comprising communications link means between said spirometer and a separate bedside receiver enabling airflow information from said computerized device of said spirometer to be provided to said bedside receiver.

12. The apparatus of claim 11, further comprising signature link means from an electronic signature device to said spirometer enabling information identifying said spirometer user to be provided to said computerized device of said spirometer, and to further be provided from said computerized device to said bedside receiver in connection and association with said airflow information from said computerized device.

13. The apparatus of claim 1, further comprising an information input device further comprising voice input means enabling said user to specify by vocalized instruction, at least one type of breathing test to be performed and at least one type of breathing measurement to be output as a result of said at least one type of breathing test.

14. The apparatus of claim 1, further comprising an information output device further comprising a voice output means for communicating to said user, instructions for using said spirometer and at least one type of breathing measurement obtained from at least one type of breathing test performed by said spirometer.

15. The apparatus of claim 1, wherein said computerized device uses said calculation of at least at least one substantially instantaneous rate of said airflow through said spirometer to calculate and output at least one breathing measurement selected from the breathing measurement group consisting of:

a substantially instantaneous rate of said airflow at at least one predetermined time; and a least one total volume of said airflow between at least one pair of different predetermined times; and at least one substantially instantaneous peak flow rate between at least one pair of different predetermined times; and at least one average flow rate between at least one pair of different predetermined times; and a plurality of substantially instantaneous rates of said airflow over a period of time between at least one pair of different predetermined times.

16. A method for measuring airflow generated by a spirometer user, comprising the steps of:

providing a rotor of said spirometer comprising a plurality of rotor blades;

said user breathing air through said spirometer thereby creating said airflow therethrough, using a mouthpiece of said spirometer;

enabling exhaled air to exit said spirometer and inhaled air to enter said spirometer through an air outlet opening of said spirometer;

providing at least one detection surface comprising part of at least one of said plurality of rotor blades;

detecting passage of said at least one detection surface past said rotation detector and generating a detection signal in response thereto using a rotation detector;

receiving said detection signal using a computerized device;

said computerized device using said detection signal to measure said airflow through said spirometer;

providing a rotor turbulence barrier surrounding said rotor;

occupying no more than 30% of a barrier cross-sectional area of said rotor turbulence barrier with a rotor cross-sectional area of said rotor; and enabling air that does not flow through said rotor turbulence barrier to flow through a remaining cross-sectional area within said spirometer outside of said rotor turbulence barrier;

thereby reducing turbulence of said airflow past said rotor while minimizing pressure drop across said rotor.

17. The method of claim 16, further comprising the steps of:

providing a modular detection and electronics section comprising said rotation detector and said computerized device;

providing a modular rotor section separate from said modular detection and electronics section, and comprising said rotor and said at least one detection surface of said tip of at least one of said blades; and allowing said rotation detector to so-detect, and not blocking said rotation detector from so-detecting, each said passage of said at least one detection surface past said rotation detector, using boundary means between said detection and electronics section, and said rotor section.

18. The method of claim 16, comprising the further steps of:

providing greater sensitivity to inhalation over exhalation by said rotor being aerodynamically flow-direction asymmetric.

19. The method of claim 16, further comprising the steps of:

connecting a rotor spindle further comprising upper and lower spindle tips, and rotating integrally with said rotor, to said rotor;

contacting said upper and lower spindle tips respectively, and supporting and providing a stable rotational origin for said rotor, using upper and lower rotor support housings within which said rotor spindle rotates; and deterring moisture due to said user's exhalation airflow from adversely lubricating said contact point and thereby undesirably causing the rotor to become more sensitive to any given airflow, using upper and lower humidity guards proximate contact points where said upper and lower spindle tips respectively contact said upper and lower rotor support housings.

20. The method of claim 16, further comprising the steps of:

connecting a rotor spindle further comprising upper and lower spindle tips, and rotating integrally with said rotor, to said rotor;

contacting said upper and lower spindle tips respectively, and supporting and providing a stable rotational origin for said rotor, using upper and lower rotor support housings within which said rotor spindle rotates; and adjusting the tightness with which said spindle and said support housing contact one another and thus the sensitivity of said rotor with respect to any given airflow, using bearing calibration means.

21. The method of claim 16, further comprising the steps of:

enabling air to flow freely while preventing particulate matter from passing into said spirometer using gross matter filter sack means proximate said mouthpiece; and indicating if said filter has already been used by providing indicator means activated in response to contact by moisture from a user's breath.

22. The method of claim 16, further comprising the steps of:

removing and replacing at least one removable and replaceable modular filtration section and at least one biostatic filter thereof without directly contacting said at least one biostatic filter, by integrally affixing said at least one biostatic filter to and within said filtration section.

23. The method of claim 22, further comprising the steps of:

enabling said spirometer to be compact and lightweight by providing said at least one biostatic filter being comprised of a compact, lightweight, microporous, accordion-type biostatic material.

24. The method of claim 17, further comprising the steps of:

orienting and positioning said mouthpiece and said air outlet opening with respect to said spirometer such that the exhalation airflow from the spirometer user exits said air outlet opening toward said user's lower body, and does not exit away from the user and toward any other individuals who may be positioned in front of the user.

25. The method of claim 16, additionally for measuring the composition of said airflow, further comprising the steps of:

obtaining data regarding the composition of air exhaled into the spirometer in comparison to ambient air using an air composition detector; and providing said data to said computerized device for any desired computation and subsequent output.

26. The method of claim 16, further comprising the steps of:

enabling airflow information from said computerized device of said spirometer to be provided to a separate bedside receiver using communications link means between said spirometer and said bedside receiver.

27. The method of claim 26, further comprising the steps of:

enabling information identifying said spirometer user to be provided to said computerized device of said spirometer, and to further be provided from said computerized device to said bedside receiver in connection and association with said airflow information from said computerized device, using signature link means from an electronic signature device to said spirometer.

28. The method of claim 16, further comprising the steps of:

enabling said user to specify by vocalized instruction, at least one type of breathing test to be performed and at least one type of breathing measurement to be output as a result of said at least one type of breathing test, using voice input means of an information input device.

29. The method of claim 16, further comprising the steps of:

communicating to said user, instructions for using said spirometer and at least one type of breathing measurement obtained from at least one type of breathing test performed by said spirometer, using voice output means of an information output device.

30. The method of claim 16, further comprising the steps of:

said computerized device using said calculation of at least at least one substantially instantaneous rate of said airflow through said spirometer to calculate and output at least one breathing measurement selected from the breathing measurement group consisting of:

a substantially instantaneous rate of said airflow at at least one predetermined time; and a least one total volume of said airflow between at least one pair of different predetermined times; and at least one substantially instantaneous peak flow rate between at least one pair of different predetermined times; and at least one average flow rate between at least one pair of different predetermined times; and a plurality of substantially instantaneous rates of said airflow over a period of time between at least one pair of different predetermined times.

31. A spirometer apparatus for measuring airflow therethrough generated by a user thereof, comprising:

a rotor comprising a plurality of rotor blades;

a mouthpiece enabling said user to breathe air through said spirometer thereby creating said airflow therethrough;

an air outlet opening enabling exhaled air to exit said spirometer and inhaled air to enter said spirometer;

at least one detection surface comprising part of at least one of said plurality of rotor blades;

a rotation detector detecting passage of said at least one detection surface past said rotation detector and generating a detection signal in response thereto;

a computerized device receiving said detection signal, and using said detection signal to measure said airflow through said spirometer;

a rotor spindle further comprising upper and lower spindle tips, connected to and rotating integrally with said rotor;

upper and lower rotor support housings contacting said upper and lower spindle tips respectively, within which said rotor spindle rotates, supporting and providing a stable rotational origin for said rotor; and upper and lower humidity guards proximate contact points where said upper and lower spindle tips respectively contact said upper and lower rotor support housings, deterring moisture due to said user's exhalation airflow from adversely lubricating said contact point and thereby undesirably causing the rotor to become more sensitive to any given airflow.

32. The apparatus of claim 31, further comprising:

a modular detection and electronics section comprising said rotation detector and said computerized device;

a modular rotor section separate from said modular detection and electronics section, and comprising said rotor and said at least one detection surface of said tip of at least one of said blades; and boundary means between said detection and electronics section, and said rotor section, allowing said rotation detector to so-detect, and not blocking said rotation detector from so-detecting, each said passage of said at least one detection surface past said rotation detector.

33. The apparatus of claim 31, wherein said rotor is aerodynamically flow-direction asymmetric so as to provide greater sensitivity to inhalation over exhalation.

34. The apparatus of claim 31, further comprising:

a rotor spindle further comprising upper and lower spindle tips, connected to and rotating integrally with said rotor;

upper and lower rotor support housings contacting said upper and lower spindle tips respectively, within which said rotor spindle rotates, supporting and providing a stable rotational origin for said rotor; and bearing calibration means for adjusting the tightness with which said spindle and said support housing contact one another and thus the sensitivity of said rotor with respect to any given airflow.

35. The apparatus of claim 31, further comprising:

gross matter filter sack means proximate said mouthpiece, enabling air to flow freely while preventing particulate matter from passing therethrough into said spirometer, and providing indicator means activated in response to contact by moisture from a user's breath to indicate if said filter has already been used.

36. The apparatus of claim 31, further comprising at least one removable and replaceable modular filtration section comprising at least one biostatic filter therein and integrally affixed thereto, providing means for a person to remove and replace said at least one filtration section and said at least one biostatic filter thereof without directly contacting said at least one biostatic filter.

37. The apparatus of claim 36, wherein said at least one biostatic filter is comprised of a compact, lightweight, microporous, accordion-type biostatic material enabling said spirometer to be compact and lightweight.

38. The apparatus of claim 31, wherein said mouthpiece and said air outlet opening are oriented and positioned with respect to said spirometer such that the exhalation airflow from the spirometer user exits said air outlet opening toward said users lower body, and does not exit away from the user and toward any other individuals who may be positioned in front of the user.

39. The apparatus of claim 31, additionally for measuring the composition of said airflow, further comprising an air composition detector obtaining data regarding the composition of air exhaled into the spirometer in comparison to ambient air, and providing said data to said computerized device for any desired computation and subsequent output.

40. The apparatus of claim 31, further comprising communications link means between said spirometer and a separate bedside receiver enabling airflow information from said computerized device of said spirometer to be provided to said bedside receiver.

41. The apparatus of claim 40, further comprising signature link means from an electronic signature device to said spirometer enabling information identifying said spirometer user to be provided to said computerized device of said spirometer, and to further be provided from said computerized device to said bedside receiver in connection and association with said airflow information from said computerized device.

42. The apparatus of claim 31, further comprising an information input device further comprising voice input means enabling said user to specify by vocalized instruction, at least one type of breathing test to be performed and at least one type of breathing measurement to be output as a result of said at least one type of breathing test.

43. The apparatus of claim 31, further comprising an information output device further comprising a voice output means for communicating to said user, instructions for using said spirometer and at least one type of breathing measurement obtained from at least one type of breathing test performed by said spirometer.

44. The apparatus of claim 31, wherein said computerized device uses said calculation of at least at least one substantially instantaneous rate of said airflow through said spirometer to calculate and output at least one breathing measurement selected from the breathing measurement group consisting of:
 a substantially instantaneous rate of said airflow at at least one predetermined time; and
 a least one total volume of said airflow between at least one pair of different predetermined times; and
 at least one substantially instantaneous peak flow rate between at least one pair of different predetermined times; and
 at least one average flow rate between at least one pair of different predetermined times; and
 a plurality of substantially instantaneous rates of said airflow over a period of time between at least one pair of different predetermined times.

45. A method for measuring airflow generated by a spirometer user, comprising the steps of:
 providing a rotor of said spirometer comprising a plurality of rotor blades;
 said user breathing air through said spirometer thereby creating said airflow therethrough, using a mouthpiece of said spirometer;
 enabling exhaled air to exit said spirometer and inhaled air to enter said spirometer through an air outlet opening of said spirometer;
 providing at least one detection surface comprising part of at least one of said plurality of rotor blades;
 detecting passage of said at least one detection surface past said rotation detector and generating a detection signal in response thereto using a rotation detector;
 receiving said detection signal using a computerized device;
 said computerized device using said detection signal to measure said airflow through said spirometer;
 connecting a rotor spindle further comprising upper and lower spindle tips, and rotating integrally with said rotor, to said rotor;
 contacting said upper and lower spindle tips respectively, and supporting and providing a stable rotational origin for said rotor, using upper and lower rotor support housings within which said rotor spindle rotates; and
 deterring moisture due to said user's exhalation airflow from adversely lubricating said contact point and thereby undesirably causing the rotor to become more sensitive to any given airflow, using upper and lower humidity guards proximate contact points where said upper and lower spindle tips respectively contact said upper and lower rotor support housings.

46. The method of claim 45, further comprising the steps of:
 providing a modular detection and electronics section comprising said rotation detector and said computerized device;
 providing a modular rotor section separate from said modular detection and electronics section, and comprising said rotor and said at least one detection surface of said tip of at least one of said blades; and
 allowing said rotation detector to so-detect, and not blocking said rotation detector from so-detecting, each said passage of said at least one detection surface past said rotation detector, using boundary means between said detection and electronics section, and said rotor section.

47. The method of claim 45, comprising the further steps of:
 providing greater sensitivity to inhalation over exhalation by said rotor being aerodynamically flow-direction asymmetric.

48. The method of claim 45, further comprising the steps of:
 connecting a rotor spindle further comprising upper and lower spindle tips, and rotating integrally with said rotor, to said rotor;
 contacting said upper and lower spindle tips respectively, and supporting and providing a stable rotational origin for said rotor, using upper and lower rotor support housings within which said rotor spindle rotates; and
 adjusting the tightness with which said spindle and said support housing contact one another and thus the sensitivity of said rotor with respect to any given airflow, using bearing calibration means.

49. The method of claim 45, further comprising the steps of:
 enabling air to flow freely while preventing particulate matter from passing into said spirometer using gross matter filter sack means proximate said mouthpiece; and indicating if said filter has already been used by providing indicator means activated in response to contact by moisture from a user's breath.

50. The method of claim 45, further comprising the steps of:

removing and replacing at least one removable and replaceable modular filtration section and at least one biostatic filter thereof without directly contacting said at least one biostatic filter, by integrally affixing said at least one biostatic filter to and within said filtration section.

51. The method of claim 50, further comprising the steps of: enabling said spirometer to be compact and lightweight by providing said at least one biostatic filter being comprised of a compact, lightweight, microporous, accordion-type biostatic material.

52. The method of claim 45, further comprising the steps of:

orienting and positioning said mouthpiece and said air outlet opening with respect to said spirometer such that the exhalation airflow from the spirometer user exits said air outlet opening toward said user's lower body, and does not exit away from the user and toward any other individuals who may be positioned in front of the user.

53. The method of claim 45, additionally for measuring the composition of said airflow, further comprising the steps of:

obtaining data regarding the composition of air exhaled into the spirometer in comparison to ambient air using an air composition detector; and providing said data to said computerized device for any desired computation and subsequent output.

54. The method of claim 45, further comprising the steps of:

enabling airflow information from said computerized device of said spirometer to be provided to a separate bedside receiver using communications link means between said spirometer and said bedside receiver.

55. The method of claim 54, further comprising the steps of:

enabling information identifying said spirometer user to be provided to said computerized device of said spirometer, and to further be provided from said computerized device to said bedside receiver in connection and association with said airflow information from said computerized device, using signature link means from an electronic signature device to said spirometer.

56. The method of claim 45, further comprising the steps of:

enabling said user to specify by vocalized instruction, at least one type of breathing test to be performed and at least one type of breathing measurement to be output as a result of said at least one type of breathing test, using voice input means of an information input device.

57. The method of claim 45, further comprising the steps of:

communicating to said user, instructions for using said spirometer and at least one type of breathing measurement obtained from at least one type of breathing test performed by said spirometer, using voice output means of an information output device.

58. The method of claim 45, further comprising the steps of:

said computerized device using said calculation of at least at least one substantially instantaneous rate of said airflow through said spirometer to calculate and output at least one breathing measurement selected from the breathing measurement group consisting of:

a substantially instantaneous rate of said airflow at at least one predetermined time; and a least one total volume of said airflow between at least one pair of different predetermined times; and at least one substantially instantaneous peak flow rate between at least one pair of different predetermined times; and at least one average flow rate between at least one pair of different predetermined times; and a plurality of substantially instantaneous rates of said airflow over a period of time between at least one pair of different predetermined times.

59. A spirometer apparatus for measuring airflow therethrough generated by a user thereof, comprising:

a rotor comprising a plurality of rotor blades;

a mouthpiece enabling said user to breathe air through said spirometer thereby creating said airflow therethrough;

an air outlet opening enabling exhaled air to exit said spirometer and inhaled air to enter said spirometer;

at least one detection surface comprising part of at least one of said plurality of rotor blades;

a rotation detector detecting passage of said at least one detection surface past said rotation detector and generating a detection signal in response thereto;

a computerized device receiving said detection signal, and using said detection signal to measure said airflow through said spirometer; and gross matter filter sack means proximate said mouthpiece, enabling air to flow freely while preventing particulate matter from passing therethrough into said spirometer, and providing indicator means activated in response to contact by moisture from a user's breath to indicate if said filter has already been used.

60. The apparatus of claim 59, further comprising:

a modular detection and electronics section comprising said rotation detector and said computerized device;

a modular rotor section separate from said modular detection and electronics section, and comprising said rotor and said at least one detection surface of said tip of at least one of said blades; and boundary means between said detection and electronics section, and said rotor section, allowing said rotation detector to so-detect, and not blocking said rotation detector from so-detecting, each said passage of said at least one detection surface past said rotation detector.

61. The apparatus of claim 59, wherein said rotor is aerodynamically flow-direction asymmetric so as to provide greater sensitivity to inhalation over exhalation.

62. The apparatus of claim 59, further comprising:

a rotor spindle further comprising upper and lower spindle tips, connected to and rotating integrally with said rotor;

upper and lower rotor support housings contacting said upper and lower spindle tips respectively, within which said rotor spindle rotates, supporting and providing a stable rotational origin for said rotor; and bearing calibration means for adjusting the tightness with which said spindle and said support housing contact one another and thus the sensitivity of said rotor with respect to any given airflow.

63. The apparatus of claim 59, further comprising at least one removable and replaceable modular filtration section comprising at least one biostatic filter therein and integrally affixed thereto, providing means for a person to remove and replace said at least one filtration section and said at least one biostatic filter thereof without directly contacting said at least one biostatic filter.

64. The apparatus of claim 63, wherein said at least one biostatic filter is comprised of a compact, lightweight, microporous, accordion-type biostatic material enabling said spirometer to be compact and lightweight.

65. The apparatus of claim 59, wherein said mouthpiece and said air outlet opening are oriented and positioned with respect to said spirometer such that the exhalation airflow from the spirometer user exits said air outlet opening toward said user's lower body, and does not exit away from the user and toward any other individuals who may be positioned in front of the user.

66. The apparatus of claim 59, additionally for measuring the composition of said airflow, further comprising an air composition detector obtaining data regarding the composition of air exhaled into the spirometer in comparison to ambient air, and providing said data to said computerized device for any desired computation and subsequent output.

67. The apparatus of claim 59, further comprising communications link means between said spirometer and a separate bedside receiver enabling airflow information from said computerized device of said spirometer to be provided to said bedside receiver.

68. The apparatus of claim 67, further comprising signature link means from an electronic signature device to said spirometer enabling information identifying said spirometer user to be provided to said computerized device of said spirometer, and to further be provided from said computerized device to said bedside receiver in connection and association with said airflow information from said computerized device.

69. The apparatus of claim 59, further comprising an information input device further comprising voice input means enabling said user to specify by vocalized instruction, at least one type of breathing test to be performed and at least one type of breathing measurement to be output as a result of said at least one type of breathing test.

70. The apparatus of claim 59, further comprising an information output device further comprising a voice output means for communicating to said user, instructions for using said spirometer and at least one type of breathing measurement obtained from at least one type of breathing test performed by said spirometer.

71. The apparatus of claim 59, wherein said computerized device uses said calculation of at least at least one substantially instantaneous rate of said airflow through said spirometer to calculate and output at least one breathing measurement selected from the breathing measurement group consisting of:
 a substantially instantaneous rate of said airflow at at least one predetermined time; and
 a least one total volume of said airflow between at least one pair of different predetermined times; and
 at least one substantially instantaneous peak flow rate between at least one pair of different predetermined times; and
 at least one average flow rate between at least one pair of different predetermined times; and
 a plurality of substantially instantaneous rates of said airflow over a period of time between at least one pair of different predetermined times.

72. A method for measuring airflow generated by a spirometer user, comprising the steps of:
 providing a rotor of said spirometer comprising a plurality of rotor blades;
 said user breathing air through said spirometer thereby creating said airflow therethrough, using a mouthpiece of said spirometer;
 enabling exhaled air to exit said spirometer and inhaled air to enter said spirometer through an air outlet opening of said spirometer;
 providing at least one detection surface comprising part of at least one of said plurality of rotor blades;
 detecting passage of said at least one detection surface past said rotation detector and generating a detection signal in response thereto using a rotation detector;
 receiving said detection signal using a computerized device;
 said computerized device using said detection signal to measure said airflow through said spirometer;
 enabling air to flow freely while preventing particulate matter from passing into said spirometer using gross matter filter sack means proximate said mouthpiece; and
 indicating if said filter has already been used by providing indicator means activated in response to contact by moisture from a user's breath.

73. The method of claim 72, further comprising the steps of:
 providing a modular detection and electronics section comprising said rotation detector and said computerized device;
 providing a modular rotor section separate from said modular detection and electronics section, and comprising said rotor and said at least one detection surface of said tip of at least one of said blades; and
 allowing said rotation detector to so-detect, and not blocking said rotation detector from so-detecting, each said passage of said at least one detection surface past said rotation detector, using boundary means between said detection and electronics section, and said rotor section.

74. The method of claim 72, comprising the further steps of:
 providing greater sensitivity to inhalation over exhalation by said rotor being aerodynamically flow-direction asymmetric.

75. The method of claim 72, further comprising the steps of:
 connecting a rotor spindle further comprising upper and lower spindle tips, and rotating integrally with said rotor, to said rotor;
 contacting said upper and lower spindle tips respectively, and supporting and providing a stable rotational origin for said rotor, using upper and lower rotor support housings within which said rotor spindle rotates; and
 adjusting the tightness with which said spindle and said support housing contact one another and thus the sensitivity of said rotor with respect to any given airflow, using bearing calibration means.

76. The method of claim 72, further comprising the steps of:
 removing and replacing at least one removable and replaceable modular filtration section and at least one biostatic filter thereof without directly contacting said at least one biostatic filter, by integrally affixing said at least one biostatic filter to and within said filtration section.

77. The method of claim 76, further comprising the steps of: enabling said spirometer to be compact and lightweight by providing said at least one biostatic filter being comprised of a compact, lightweight, microporous, accordion-type biostatic material.

78. The method of claim 72, further comprising the steps of: orienting and positioning said mouthpiece and said air outlet opening with respect to said spirometer such that the exhalation airflow from the spirometer user exits said air outlet opening toward said user's lower body, and does not exit away from the user and toward any other individuals who may be positioned in front of the user.

79. The method of claim 72, additionally for measuring the composition of said airflow, further comprising the steps of:

obtaining data regarding the composition of air exhaled into the spirometer in comparison to ambient air using an air composition detector; and providing said data to said computerized device for any desired computation and subsequent output.

80. The method of claim 72, further comprising the steps of:

enabling airflow information from said computerized device of said spirometer to be provided to a separate bedside receiver using communications link means between said spirometer and said bedside receiver.

81. The method of claim 80, further comprising the steps of:

enabling information identifying said spirometer user to be provided to said computerized device of said spirometer, and to further be provided from said computerized device to said bedside receiver in connection and association with said airflow information from said computerized device, using signature link means from an electronic signature device to said spirometer.

82. The method of claim 72, further comprising the steps of:

enabling said user to specify by vocalized instruction, at least one type of breathing test to be performed and at least one type of breathing measurement to be output as a result of said at least one type of breathing test, using voice input means of an information input device.

83. The method of claim 72, further comprising the steps of:

communicating to said user, instructions for using said spirometer and at least one type of breathing measurement obtained from at least one type of breathing test performed by said spirometer, using voice output means of an information output device.

84. The method of claim 72, further comprising the steps of:

said computerized device using said calculation of at least at least one substantially instantaneous rate of said airflow through said spirometer to calculate and output at least one breathing measurement selected from the breathing measurement group consisting of:

a substantially instantaneous rate of said airflow at at least one predetermined time; and a least one total volume of said airflow between at least one pair of different predetermined times; and at least one substantially instantaneous peak flow rate between at least one pair of different predetermined times; and at least one average flow rate between at least one pair of different predetermined times; and a plurality of substantially instantaneous rates of said airflow over a period of time between at least one pair of different predetermined times.

85. A spirometer apparatus for measuring airflow therethrough generated by a user thereof, comprising:

a rotor comprising a plurality of rotor blades;

a mouthpiece enabling said user to breathe air through said spirometer thereby creating said airflow therethrough;

an air outlet opening enabling exhaled air to exit said spirometer and inhaled air to enter said spirometer;

at least one detection surface comprising part of at least one of said plurality of rotor blades;

a rotation detector detecting passage of said at least one detection surface past said rotation detector and generating a detection signal in response thereto;

a computerized device receiving said detection signal, and using said detection signal to measure said airflow through said spirometer; and at least one removable and replaceable modular filtration section comprising at least one biostatic filter therein and integrally affixed thereto, providing means for a person to remove and replace said at least one filtration section and said at least one biostatic filter thereof without directly contacting said at least one biostatic filter.

86. The apparatus of claim 85, further comprising:

a modular detection and electronics section comprising said rotation detector and said computerized device;

a modular rotor section separate from said modular detection and electronics section, and comprising said rotor and said at least one detection surface of said tip of at least one of said blades; and boundary means between said detection and electronics section, and said rotor section, allowing said rotation detector to so-detect, and not blocking said rotation detector from so-detecting, each said passage of said at least one detection surface past said rotation detector.

87. The apparatus of claim 85, wherein said rotor is aerodynamically flow-direction asymmetric so as to provide greater sensitivity to inhalation over exhalation.

88. The apparatus of claim 85, further comprising:

a rotor spindle further comprising upper and lower spindle tips, connected to and rotating integrally with said rotor;

upper and lower rotor support housings contacting said upper and lower spindle tips respectively, within which said rotor spindle rotates, supporting and providing a stable rotational origin for said rotor; and bearing calibration means for adjusting the tightness with which said spindle and said support housing contact one another and thus the sensitivity of said rotor with respect to any given airflow.

89. The apparatus of claim 85, wherein said at least one biostatic filter is comprised of a compact, lightweight, microporous, accordion-type biostatic material enabling said spirometer to be compact and lightweight.

90. The apparatus of claim 85, wherein said mouthpiece and said air outlet opening are oriented and positioned with respect to said spirometer such that the exhalation airflow from the spirometer user exits said air outlet opening toward said user's lower body, and does not exit away from the user and toward any other individuals who may be positioned in front of the user.

91. The apparatus of claim 85, additionally for measuring the composition of said airflow, further comprising an air composition detector obtaining data regarding the composition of air exhaled into the spirometer in comparison to ambient air, and providing said data to said computerized device for any desired computation and subsequent output.

92. The apparatus of claim 85, further comprising communications link means between said spirometer and a separate bedside receiver enabling airflow information from said computerized device of said spirometer to be provided to said bedside receiver.

93. The apparatus of claim 92, further comprising signature link means from an electronic signature device to said spirometer enabling information identifying said spirometer user to be provided to said computerized device of said spirometer, and to further be provided from said computerized device to said bedside receiver in connection and association with said airflow information from said computerized device.

94. The apparatus of claim 85, further comprising an information input device further comprising voice input means enabling said user to specify by vocalized instruction, at least one type of breathing test to be performed and at least one type of breathing measurement to be output as a result of said at least one type of breathing test.

95. The apparatus of claim 85, further comprising an information output device further comprising a voice output means for communicating to said user, instructions for using said spirometer and at least one type of breathing measurement obtained from at least one type of breathing test performed by said spirometer.

96. The apparatus of claim 85, wherein said computerized device uses said calculation of at least at least one substantially instantaneous rate of said airflow through said spirometer to calculate and output at least one breathing measurement selected from the breathing measurement group consisting of:
   a substantially instantaneous rate of said airflow at at least one predetermined time; and
   a least one total volume of said airflow between at least one pair of different predetermined times; and
   at least one substantially instantaneous peak flow rate between at least one pair of different predetermined times; and
   at least one average flow rate between at least one pair of different predetermined times; and
   a plurality of substantially instantaneous rates of said airflow over a period of time between at least one pair of different predetermined times.

97. A method for measuring airflow generated by a spirometer user, comprising the steps of:
   providing a rotor of said spirometer comprising a plurality of rotor blades;
   said user breathing air through said spirometer thereby creating said airflow therethrough, using a mouthpiece of said spirometer;
   enabling exhaled air to exit said spirometer and inhaled air to enter said spirometer through an air outlet opening of said spirometer;
   providing at least one detection surface comprising part of at least one of said plurality of rotor blades;
   detecting passage of said at least one detection surface past said rotation detector and generating a detection signal in response thereto using a rotation detector;
   receiving said detection signal using a computerized device;
   said computerized device using said detection signal to measure said airflow through spirometer; and
   removing and replacing at least one removable and replaceable modular filtration section and at least one biostatic filter thereof without directly contacting said at least one biostatic filter, by integrally affixing said at least one biostatic filter to and within said filtration section.

98. The method of claim 97, further comprising the steps of:
   providing a modular detection and electronics section comprising said rotation detector and said computerized device;
   providing a modular rotor section separate from said modular detection and electronics section, and comprising said rotor and said at least one detection surface of said tip of at least one of said blades; and
   allowing said rotation detector to so-detect, and not blocking said rotation detector from so-detecting, each said passage of said at least one detection surface past said rotation detector, using boundary means between said detection and electronics section, and said rotor section.

99. The method of claim 97, comprising the further steps of:
   providing greater sensitivity to inhalation over exhalation by said rotor being aerodynamically flow-direction asymmetric.

100. The method of claim 97, further comprising the steps of:
   connecting a rotor spindle further comprising upper and lower spindle tips, and rotating integrally with said rotor, to said rotor;
   contacting said upper and lower spindle tips respectively, and supporting and providing a stable rotational origin for said rotor, using upper and lower rotor support housings within which said rotor spindle rotates; and
   adjusting the tightness with which said spindle and said support housing contact one another and thus the sensitivity of said rotor with respect to any given airflow, using bearing calibration means.

101. The method of claim 97, further comprising the steps of: enabling said spirometer to be compact and lightweight by providing said at least one biostatic filter being comprised of a compact, lightweight, microporous, accordion-type biostatic material.

102. The method of claim 97, further comprising the steps of: orienting and positioning said mouthpiece and said air outlet opening with respect to said spirometer such that the exhalation airflow from the spirometer user exits said air outlet opening toward said user's lower body, and does not exit away from the user and toward any other individuals who may be positioned in front of the user.

103. The method of claim 99, additionally for measuring the composition of said airflow, further comprising the steps of:
   obtaining data regarding the composition of air exhaled into the spirometer in comparison to ambient air using an air composition detector; and
   providing said data to said computerized device for any desired computation and subsequent output.

104. The method of claim 97, further comprising the steps of:
   enabling airflow information from said computerized device of said spirometer to be provided to a separate bedside receiver using communications link means between said spirometer and said bedside receiver.

105. The method of claim 104, further comprising the steps of:

enabling information identifying said spirometer user to be provided to said computerized device of said spirometer, and to further be provided from said computerized device to said bedside receiver in connection and association with said airflow information from said computerized device, using signature link means from an electronic signature device to said spirometer.

106. The method of claim 97, further comprising the steps of:

enabling said user to specify by vocalized instruction, at least one type of breathing test to be performed and at least one type of breathing measurement to be output as a result of said at least one type of breathing test, using voice input means of an information input device.

107. The method of claim 97, further comprising the steps of:

communicating to said user, instructions for using said spirometer and at least one type of breathing measurement obtained from at least one type of breathing test performed by said spirometer, using voice output means of an information output device.

108. The method of claim 97, further comprising the steps of:

said computerized device using said calculation of at least at least one substantially instantaneous rate of said airflow through said spirometer to calculate and output at least one breathing measurement selected from the breathing measurement group consisting of:

a substantially instantaneous rate of said airflow at at least one predetermined time; and a least one total volume of said airflow between at least one pair of different predetermined times; and at least one substantially instantaneous peak flow rate between at least one pair of different predetermined times; and at least one average flow rate between at least one pair of different predetermined times; and a plurality of substantially instantaneous rates of said airflow over a period of time between at least one pair of different predetermined times.

* * * * *